(12) United States Patent
Leyh

(10) Patent No.: US 8,211,097 B2
(45) Date of Patent: Jul. 3, 2012

(54) OPTIMIZING RF POWER SPATIAL DISTRIBUTION USING FREQUENCY CONTROL

(75) Inventor: Greg Leyh, Brisbane, CA (US)

(73) Assignee: Cutera, Inc., Brisbane, CA (US)

( * ) Notice: Subject to any disclaimer, the term of this patent is extended or adjusted under 35 U.S.C. 154(b) by 521 days.

(21) Appl. No.: 12/371,103

(22) Filed: Feb. 13, 2009

(65) Prior Publication Data

US 2010/0211061 A1  Aug. 19, 2010

(51) Int. Cl.
  *A61B 18/04* (2006.01)
(52) U.S. Cl. ........................................................ 606/31
(58) Field of Classification Search ............... 606/33, 606/41, 31, 34
  See application file for complete search history.

(56) References Cited

U.S. PATENT DOCUMENTS

| | | | |
|---|---|---|---|
| 3,683,923 A | 8/1972 | Anderson | |
| 4,140,130 A | 2/1979 | Storm, III | |
| 4,200,104 A | 4/1980 | Harris | |
| 4,315,510 A * | 2/1982 | Kihn | 606/33 |
| 4,416,276 A | 11/1983 | Newton et al. | |
| 4,416,277 A | 11/1983 | Newton et al. | |
| 4,527,550 A | 7/1985 | Ruggera et al. | |
| 4,597,379 A * | 7/1986 | Kihn et al. | 606/40 |
| 4,657,015 A | 4/1987 | Irnich | |
| 4,776,350 A | 10/1988 | Grossman et al. | |
| 4,848,335 A | 7/1989 | Manes | |
| 5,143,063 A | 9/1992 | Fellner | |
| 5,383,917 A * | 1/1995 | Desai et al. | 607/102 |
| 5,480,399 A | 1/1996 | Hebborn | |
| 5,542,916 A * | 8/1996 | Hirsch et al. | 604/22 |
| 5,836,942 A | 11/1998 | Netherly et al. | |
| 5,837,001 A * | 11/1998 | Mackey | 607/102 |
| 6,063,075 A | 5/2000 | Mihori | |
| 6,083,221 A | 7/2000 | Fleenor et al. | |
| 6,240,323 B1 | 5/2001 | Calenzo, Sr. et al. | |
| 6,258,085 B1 | 7/2001 | Eggleston | |

(Continued)

OTHER PUBLICATIONS

U.S. Appl. No. 11/966,895, filed Dec. 28, 2007, by Greg Leyh, entitled "High Conductivity Inductively Equalized Electrodes and Methods".

*Primary Examiner* — Christopher D Koharski
*Assistant Examiner* — Diva K Chander
(74) *Attorney, Agent, or Firm* — Morrison & Foerster LLP

(57) ABSTRACT

An electro-surgical system actively maintains an optimal heating profile at the electrode-patient contact surface under varying load resistivity, thereby reducing the risk of burns and maximizing patient comfort at a given power level. A set of temperature sensors is integrated within the electrode assembly of the electrosurgical system. The sensors are located both at the center and the edges of the electrode. The sensors are thermally coupled to the electrode-patient contact surface and have a time response that is short compared to the thermal time constraints of the tissue. Some degree of signal processing may take place at the sensor, inside the transducer assembly. As RF power is applied, a control loop monitors the temperature at the center and edges of the electrode. If the edge temperature of the electrode is high compared to its center temperature, then the control loop increases the operating frequency, effectively driving heat towards the center of the electrode. Conversely, if the edge temperature of the electrode is low compared to its center temperature, then the control loop decreases the operating frequency, effectively driving heat towards the edges of the electrode. By actively adjusting the operating frequency in this way, the control loop maintains any chosen heating profile at the electrode-patient contact surface.

8 Claims, 10 Drawing Sheets

U.S. PATENT DOCUMENTS

| | | |
|---|---|---|
| 6,413,255 B1 | 7/2002 | Stern |
| 6,488,678 B2 | 12/2002 | Sherman |
| 6,544,258 B2 | 4/2003 | Fleenor et al. |
| 6,635,056 B2 * | 10/2003 | Kadhiresan et al. ............ 606/34 |
| 6,730,078 B2 * | 5/2004 | Simpson et al. ................ 606/34 |
| 6,860,881 B2 | 3/2005 | Sturm et al. |
| 6,936,047 B2 * | 8/2005 | Nasab et al. .................... 606/34 |
| 7,151,964 B2 | 12/2006 | Desai et al. |
| 7,169,145 B2 | 1/2007 | Isaacson et al. |
| 7,250,047 B2 | 7/2007 | Anderson et al. |
| 7,278,991 B2 * | 10/2007 | Morris et al. ................... 606/41 |
| 7,419,487 B2 * | 9/2008 | Johnson et al. ................. 606/41 |
| 2002/0058938 A1 | 5/2002 | Cosmescu |
| 2002/0072664 A1 | 6/2002 | Katzenmaier et al. |
| 2002/0147467 A1 | 10/2002 | Bernabei |
| 2003/0163185 A1 | 8/2003 | Carson |
| 2003/0199862 A1 * | 10/2003 | Simpson et al. ................ 606/34 |
| 2005/0033278 A1 * | 2/2005 | McClurken et al. ............ 606/41 |
| 2006/0036300 A1 | 2/2006 | Kreindel |
| 2006/0074411 A1 | 4/2006 | Carmel et al. |
| 2006/0079872 A1 | 4/2006 | Eggleston |
| 2006/0224150 A1 | 10/2006 | Arts et al. |
| 2006/0235286 A1 | 10/2006 | Stone et al. |
| 2007/0049914 A1 * | 3/2007 | Eggleston ....................... 606/32 |
| 2007/0167942 A1 | 7/2007 | Rick |
| 2007/0203482 A1 | 8/2007 | Ein-Gal |
| 2007/0219546 A1 * | 9/2007 | Mody et al. .................... 606/27 |
| 2007/0225697 A1 * | 9/2007 | Shroff et al. ................... 606/33 |
| 2007/0239075 A1 | 10/2007 | Rosenberg et al. |
| 2007/0244478 A1 | 10/2007 | Bahney |
| 2007/0282318 A1 | 12/2007 | Spooner et al. |
| 2008/0312651 A1 | 12/2008 | Pope et al. |
| 2009/0171341 A1 | 7/2009 | Pope et al. |
| 2009/0171344 A1 | 7/2009 | Pontis |
| 2009/0171346 A1 | 7/2009 | Leyh |
| 2009/0306647 A1 | 12/2009 | Leyh et al. |
| 2009/0318917 A1 | 12/2009 | Leyh et al. |
| 2010/0022999 A1 | 1/2010 | Gollnick et al. |
| 2010/0094271 A1 * | 4/2010 | Ward et al. ..................... 606/33 |
| 2010/0211061 A1 | 8/2010 | Leyh |

* cited by examiner

OPTIMIZING RF POWER SPATIAL DISTRIBUTION USING FREQUENCY CONTROL

FIELD OF THE INVENTION

The present invention relates generally to apparatus and methods for electro-surgery and, in particular, to utilization of active frequency control to maintain an optimal spatial heating profile for an electro-surgical apparatus.

BACKGROUND OF THE INVENTION

Eddy-current effects tend to force high frequency RF currents towards the outer surface of any conductor, biological or metal. This tendency, known as the "skin effect," is dependent upon the bulk resistivity of the conductor and the operating frequency.

At the electrode-patient contact in electro-surgical applications, the skin effect tends to force currents towards the edge of the electrode, resulting in significant tissue heating at the electrode edges. This is a major concern in electro-surgical treatments since second or third degree burns are possible, particularly if the patient is anesthetized.

Adding a distributed reactance to the electrode contact surface significantly reduces burn risks by cancelling the skin effect to first order, producing a considerably more uniform heating profile. However, since bulk resistivity is a direct factor in the skin effect equation, changes in the tissue resistivity surrounding the electrode can still significantly alter the heating profile during treatment if the operating frequency is fixed.

There are several known approaches to addressing this problem. In one such approach, a fixed operating frequency is selected from multi-dimensional lookup tables, based upon measurements of fat thickness and other empirical parameters. In a second approach, treatment is performed at a fixed power level or power cycling profile and is terminated upon indication of excessive skin temperature. In a third approach, treatment is performed at a fixed power level or power cycling profile and is terminated upon patient request.

It is, however, desirable to have available a treatment system and method that eliminates the need for lookup tables and actively maintains an optimal spatial heating profile under varying load resistivity, thereby reducing the risk of burns and maximizing patient comfort at a given power level.

SUMMARY OF THE INVENTION

In accordance with the present invention, a set of temperature sensors is integrated within the electrode assembly of an electro-surgical system. The sensors are located both at the center and the edge of the electrode. The sensors are thermally coupled to the electrode-patient contact surface and have a time response that is short compared to the thermal time constraints of the tissue. Some degree of signal processing may take place at the sensor, inside the transducer assembly. As RF power is applied, a control loop monitors the temperature at the center and edge of the electrode. If the edge temperature of the electrode is high compared to its center temperature, then the control loop increases the operating frequency, effectively driving heat towards the center of the electrode. Conversely, if the edge temperature of the electrode is low compared to its center temperature, then the control loop decreases the operating frequency, effectively moving heat towards the edges of the electrode. By actively adjusting the operating frequency in this way, the control loop maintains any chosen heating profile at the electrode-patient contact surface. The control system can use either a state machine or a proportional-integral-derivative (PID) algorithm for the frequency control loop.

The features and advantages of the various aspects of the present invention will be more fully understood and appreciated upon consideration of the following detailed description of the invention and the accompanying drawings, which set forth an illustrative embodiment in which the concepts of the invention are utilized.

DETAILED DESCRIPTION OF THE INVENTION

The following detailed description is of the best currently contemplated modes of carrying out the invention. The invention is described in the context of subject matter disclosed in co-pending and commonly-assigned application Ser. No. 11/966,895, filed on Dec. 28, 2007, by Greg Leyh. However, the description is not to be taken in a limiting sense, but is made merely for the purpose of illustrating the general principles of the invention, since the scope of the invention is best defined by the appended claims.

Broadly, the present invention provides apparatus and methods for performing electro-surgical procedures in a safe and effective manner while preventing the uneven treatment of a target tissue and/or patient burns. Patient burns are known to occur using apparatus and methods of the prior art due to uneven distribution of electric current density over the surface of conventional return electrodes. In contrast to prior art devices, a set of temperature sensors is integrated within the electrode assembly of the electro-surgical instrument. The sensors are located both at the center and the edges of the electrode. The sensors are thermally coupled to the electrode patient contact surface and have a time response that is short compared to the thermal time constraints of the tissue. Some degree of signal processing may take place at the sensor, inside the transducer assembly. As RF power is applied, a control loop monitors the temperature at the center and at the edges of the electrode. If the edge temperature of the electrode is high compared to its center temperature, then the control loop increases the operating frequency, effectively driving heat towards the center of the electrode. Conversely, if the edge temperature of the electrode is low compared to its center temperature, then the control loop decreases the operating frequency, effectively driving heat toward the edges of the electrode. By actively adjusting the operating frequency, the control loop maintains any chosen heating profile at the electrode-patient contact surface, thereby preventing patient burns.

The apparatus and methods of the present invention may find many applications, including a broad range of electro-surgical procedures and other biomedical procedures. Such procedures may involve, for example, without limitation: cutting and/or coagulation during general surgery, as well as various cosmetic procedures, and the like.

Figure 1:
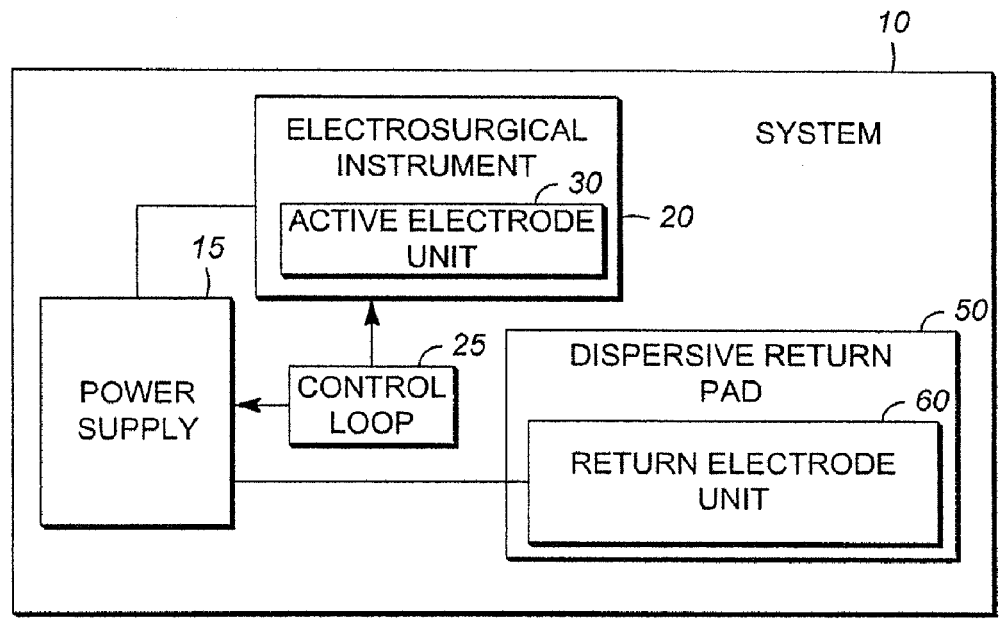
FIG. 1 is a block diagram schematically representing an electro-surgical apparatus, according to an embodiment of the invention.

FIG. 1 is a block diagram schematically representing an electro-surgical apparatus according to an embodiment of the invention. Electro-surgical system 10 of FIG. 1 may include an electro-surgical generator or power supply 15, an electro-surgical instrument 20, a control loop 25, and a dispersive return pad 50. Electro-surgical system 10 may be configured for monopolar electro-surgery. Power supply 15 may be configured for supplying electrical energy, such as radiofrequency (RF) alternating current, to electro-surgical instrument 20. Electro-surgical instrument 20 may be configured for electrical coupling to power supply 15, and for applying electrical energy to a patient's body or tissue(s) during a procedure. Embodiments of an electro-surgical instrument 20 are schematically represented hereinbelow (see, e.g., FIGS. 8 and 11, infra). Dispersive return pad 50 may include a return electrode unit 60. Dispersive return pad 50 may be configured for promoting contact between return electrode unit 60 and a patient's body.

Figure 2:
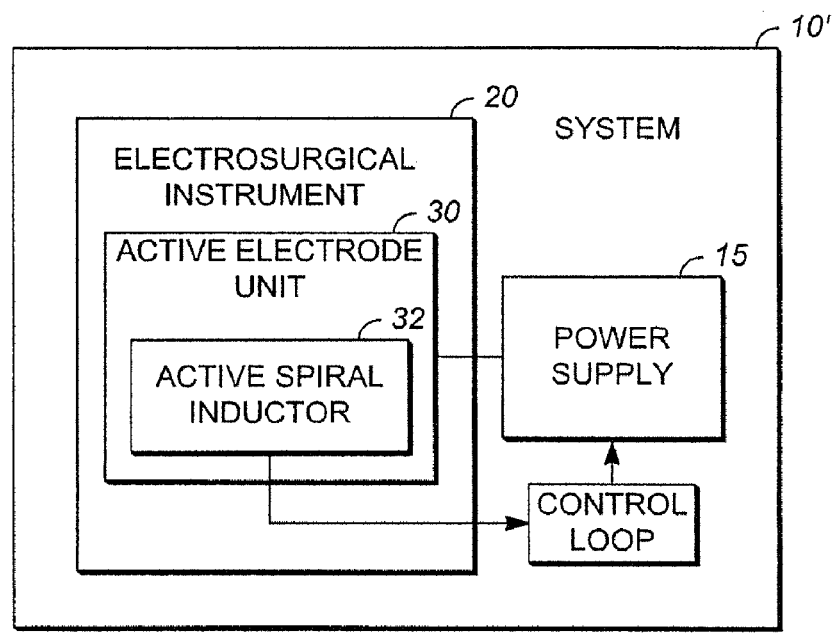
FIG. 2 is a block diagram schematically representing an electro-surgical apparatus including an active electrode unit having a spiral inductor, according to an alternate embodiment of the invention.

FIG. 2 is a block diagram schematically representing an electro-surgical apparatus according to another embodiment of the invention. Electro-surgical system 10' of FIG. 2 may include an electro-surgical instrument 20 having an active electrode unit 30. Active electrode unit 30 may be configured for electrical coupling to power supply 15. Active electrode unit 30 may include at least one spiral inductor, which may be referred to herein as an active spiral inductor 32. Active spiral inductor(s) 32 may be configured for applying electrical energy to a patient's body (see, for example, FIG. 11). Active spiral inductor 32 may have suitable self-inductance for promoting the even distribution of electrical current density thereover while active electrode unit 60 is applying electrical energy to the patient's body during a procedure. Active spiral inductor 32 may comprise one or more spirals of electrically conductive metal (see, e.g., FIGS. 4A-C, 5, 6A-B, and 9C). Active spiral inductor 32 is connected to power supply 15 via control loop 25.

Figure 3:
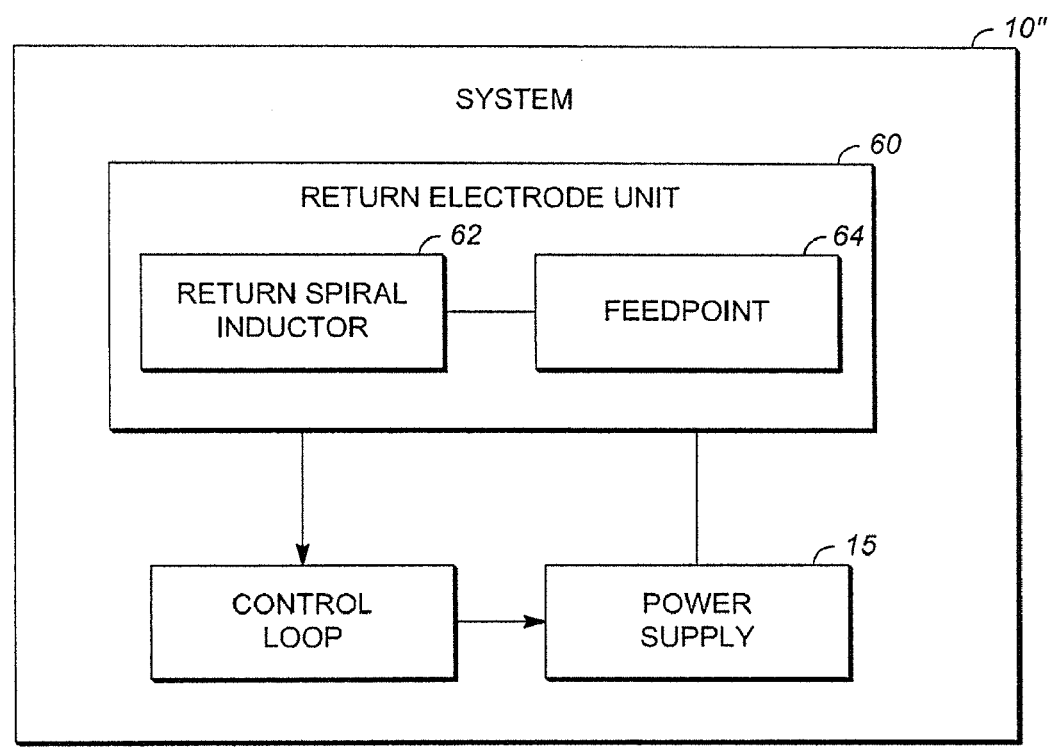
FIG. 3 is a block diagram schematically representing an electro-surgical apparatus including a return electrode unit having a spiral inductor, according to another alternate embodiment of the invention.

FIG. 3 is a block diagram schematically representing an electro-surgical apparatus according to an embodiment of the invention. The electro-surgical system 10" of FIG. 3 may include a return electrode unit 60, a power supply 15 and a control loop 25. Return electrode unit 60 may include a spiral inductor, which may be referred to herein as a return spiral inductor 62, and a feedpoint 64 electrically coupled to return spiral inductor 62. In an embodiment, return spiral inductor 62 may comprise a plurality of spirals of electrically conductive metal, wherein the plurality of spirals are stacked and electrically interconnected (see, for example, FIGS. 4A-C, 5 and 6A-B). Return spiral inductor 62 may be configured for contacting a patient's body. Return spiral inductor 62 may have suitable self-inductance for promoting the even distribution of electrical current density thereover while return electrode unit 60 is receiving electrical energy from the patient's body during a procedure.

Electrically Conductive Spirals and Spiral Inductors

There now follows a description of electrically conductive spirals and spiral inductors that may be used in a broad range of applications in accordance with the concepts of the invention.

Figure 4A:
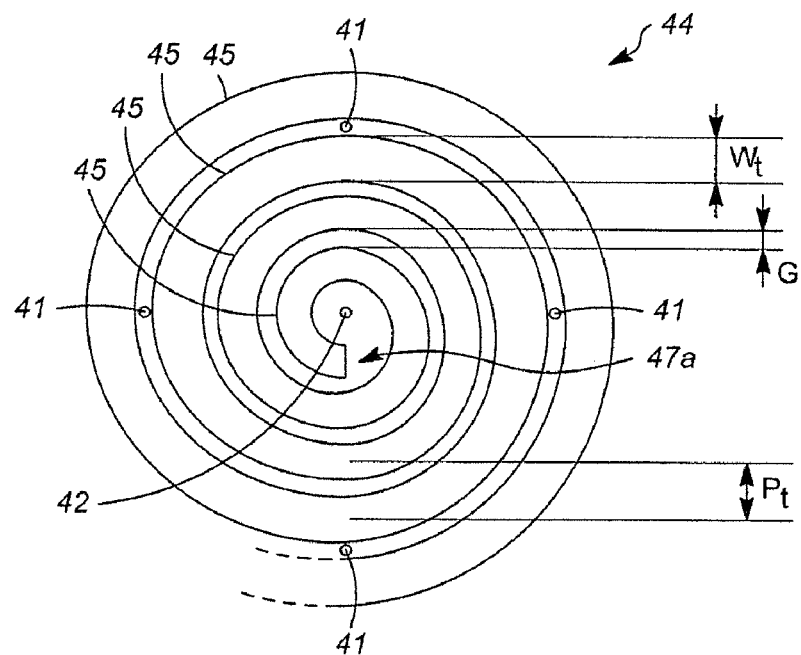
FIG. 4A schematically represents a spiral for a spiral inductor, as seen in plan view, according to another embodiment of the invention.

FIG. 4A schematically represents a spiral of electrically conductive material, as seen in plan view. Spiral 44 may include a plurality of turns 45 and an inner terminus 47a. Only a few of the radially inner turns of spiral 44 are shown in FIG. 4A, whereas spiral 44 may comprise from about 10 to 200 or more turns, typically from about 20 to 150 turns, often from about 30 to 150 turns, and usually from about 40 to 120 turns. As an example, spiral 44 may comprise a spiral trace of an electrically conductive metal, such as Cu, Al, or various alloys, as non-limiting examples. In an embodiment, spiral 44 may comprise a filament of the electrically conductive metal, wherein the filament may be disposed on a support layer 24. In an embodiment, spiral 44 may be formed (e.g. onto a substrate) by a printing process or a printing-like process.

As shown in FIG. 4A, spiral 44 may have a pitch, Pt, representing a radial distance between the radial midpoints of adjacent turns 45. The pitch of spiral 44 may be in the range of from about 0.1 mm to 10 mm or more, typically from about 0.2 mm to 9 mm, often from about 0.25 to 5 mm, and in some embodiments from about 0.3 to 1.5 mm. In an embodiment, the pitch of spiral 44 may be constant or substantially constant. In other embodiments, the pitch of spiral 44 may vary (see, e.g., FIGS. 4B-C).

Turns 45 of spiral 44 may have a width, Wt, wherein the width, Wt is a radial distance across each turn 45. The width of each of turns 45 may typically be in the range of from about 0.05 mm to 10 mm or more, typically from about 0.15 to 9 mm, often from about 0.2 to 5 mm, and in some embodiments from about 0.25 to 1.5 mm. In an embodiment, the width of the various turns 45 may be constant or substantially constant. In other embodiments, the width of turns 45 may vary (see, e.g., FIGS. 4B-C). A profile or cross-sectional shape of turns 45 may be substantially rectangular or rounded; typically the width of each turn 45 may be greater than its height.

A gap, G may exist between adjacent turns 45 of spiral 44, wherein the gap may represent a radial distance between opposing edges of adjacent turns 45. The gap is typically less than the pitch, usually the gap is substantially less than the pitch, and often the gap is considerably less than the pitch. The gap between turns 45 of spiral 44 may typically be in the range of from about 0.1 mm to 0.5 mm, usually from about 0.15 to 0.4 mm, and often from about 0.15 to 0.3 mm. In an embodiment, the gap between adjacent turns 45 may be constant or substantially constant, even though the pitch may be variable (see, e.g., FIGS. 4B-C). The gap between turns 45 may be air, as a non-limiting example.

Figure 4B:
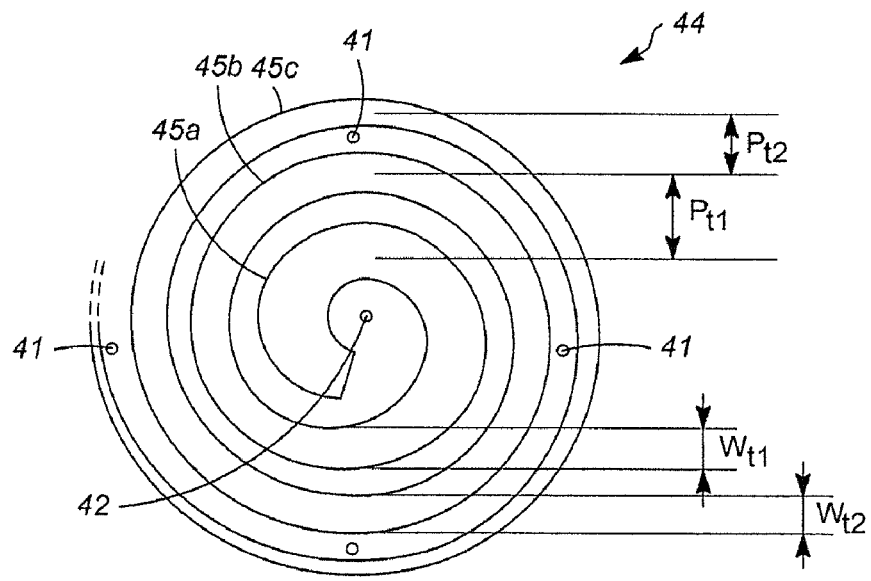
FIG. 4B schematically represents a spiral of a spiral inductor having a variable pitch, as seen in plan view, according to another embodiment of the invention.

FIG. 4B schematically represents a spiral 44 of electrically conductive material, as seen in plan view, according to another embodiment of the invention. As shown in FIG. 4B, spiral 44 may have a variable pitch, wherein the pitch (shown as Pt1, Pt2) may increase in a radially inward direction. For example, in the embodiment of FIG. 4B the following relationship may exist: Pt1>Pt2. As also shown in FIG. 4B, turns 45 of spiral 44 may have a variable width, Wt wherein the width of first and second turns 45a, 45b, respectively (shown as Wt1, Wt2) may also increase in a radially inward direction, wherein Wt1>Wt2.

Figure 4C:
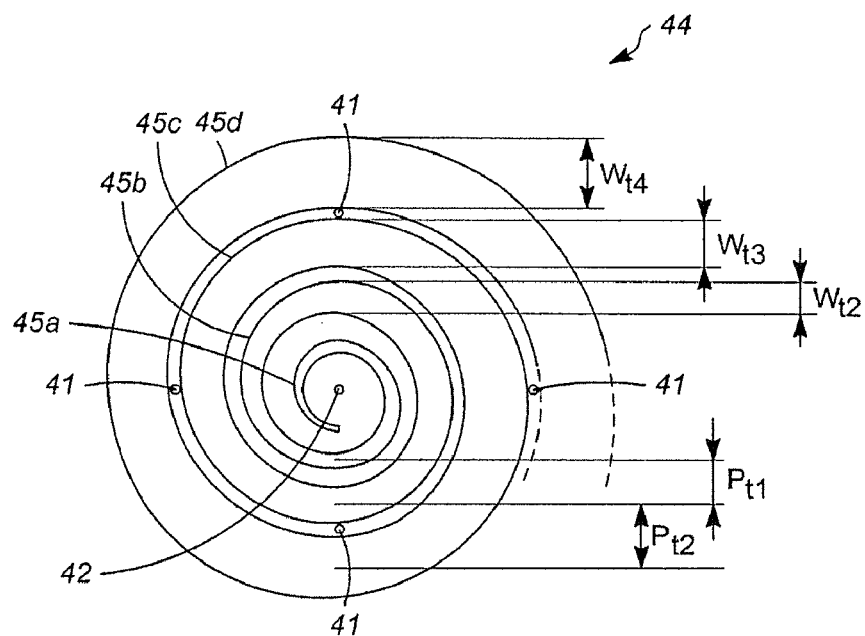
FIG. 4C schematically represents a spiral of a spiral inductor, as seen in side view, according to another embodiment of the invention.

FIG. 4C schematically represents a spiral 44 of electrically conductive material, as seen in plan view, according to another embodiment of the invention. As shown in FIG. 4C, spiral 44 may have a variable pitch, wherein the pitch (shown as Pt1, Pt2) may increase in a radially outward direction. For example, in the embodiment of FIG. 4C the following relationship may exist: Pt1<Pt2. As also shown in FIG. 4C, turns 45 of spiral 44 may have a variable width, Wt wherein the width (shown as Wt2, Wt3, Wt4) may also increase in a radially outward direction, wherein Wt2<Wt3<Wt4.

With further reference to FIGS. 4B-C, in an embodiment wherein the pitch of spiral 44 may be variable (i.e., the pitch may increase or decrease in a radial direction), the width of the turns, the pitch, and the gap between opposing edges of adjacent turns, may be substantially as described hereinabove with reference to FIG. 4A. In various embodiments of the invention, the pitch of spiral 44 may be variable over all or part of spiral 44, wherein the pitch over all or part of spiral 44 may increase or decrease in a radial direction according to either a continuous or discontinuous gradient. In an embodiment, the variation in pitch and width between adjacent turns 45 of spiral 44 may extend over 150 or more turns 45 of spiral 44.

Spiral 44 of the invention may be at least substantially planar. Coils of spiral 44 may be laterally or radially spaced-apart. Spirals 44 of the invention may be configured such that the width of a given turn of spiral 44 is much greater than the gap between that turn and an adjacent turn (see, e.g., FIG. 4A). Therefore, most of the external surface area of a spiral inductor 32/62 formed by spiral 44 may be occupied by electrically conductive metal of spiral 44 (see, e.g., FIGS. 7A-B). Although spirals 44 of FIGS. 4A-C are shown as being at least substantially circular in configuration, other configurations including oval, square, rectangular, and the like, are also within the scope of the invention. In a square or rectangular configuration of spiral 44, acute angles and right angles may be avoided; for example, in some embodiments spiral 44 may have obtuse angles (see, e.g., FIG. 7B).

In accordance with the concepts of the present invention spiral 44 includes at least one, and preferably a plurality, of edge temperature sensors 41 that are mounted to monitor the edge temperature at an edge region of the of the spiral 44 (see FIGS. 4A-4C). Spiral 44 also includes at least one center temperature sensor 42 mounted to monitor the center temperature of a center region of the spiral 44. The edge temperature sensors 41 and the center temperature sensor 42 provide corresponding edge temperature signals and center temperature signal, respectively, to the control loop 25 (see FIGS. 4A-4C). As stated above, the control loop 25 compares the received edge temperature signals and the received center temperature signal and provides a frequency control signal to the power generator 15. The control loop 25 may utilize, for example, a state machine or a proportional-integral-derivative (PID) algorithm to provide the frequency control signal to the power generator 15.

In further accordance with the concepts of the present invention, in the event that the edge temperature of the spiral 44 is high compared to the center temperature of the spiral 44, then the control loop 25 will provide a frequency control signal that causes the power generator 15 to increase the operating frequency, thereby effectively driving heat to the center of the spiral 44; in the event that the center temperature of the spiral 44 is high compared to the edge temperature of the spiral 44, then the control loop 25 will provide a frequency control signal that causes the power generator 15 to decrease the operating frequency, thereby effectively driving heat to the edge region of the spiral 44.

Figure 5:
FIG. 5 schematically represents a multi-layer spiral inductor, as seen in side view, according to another embodiment of the invention.

FIG. 5 schematically represents a multi-layer spiral inductor having a plurality of vertically stacked electrically conductive spirals, as seen in side view. As shown, spiral inductor 32/62 may include three, vertically stacked spiral layers 46. Each of spiral layers 46 may include a spiral 44 of electrically conductive metal (see, e.g., FIG. 4A), wherein each spiral 44 may be disposed on a support layer (not shown). Spiral inductor 32/62 may comprise an active spiral inductor 32 for an active electrode unit 30 (see, e.g., FIGS. 9A-C), or a return spiral inductor 62 for a return electrode unit 60 (see, e.g., FIGS. 13B-D).

Although three layers are shown in FIG. 5, other numbers of layers are also within the scope of the invention. Typically, spiral inductor 32/62 may include about two (2) to four (4) spiral layers. In general, the more spiral layers, the greater the inductive effect per unit area of spiral inductor 32/62.

Figure 6A:
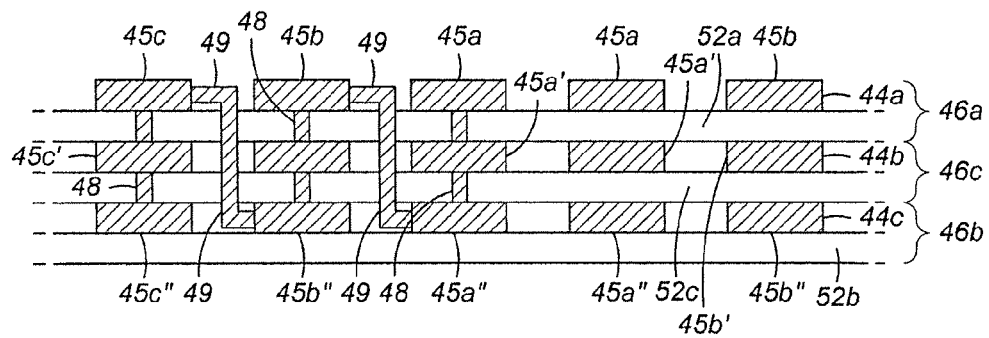
FIG. 6A schematically represents a spiral inductor, including a plurality of vertically stacked spirals, having electrical connections between turns of each spiral, as seen in side view, according to another embodiment of the invention.

FIG. 6A schematically represents a central portion of a multi-layer spiral inductor, as seen in side view. Spiral inductor 32/62 may be a component of an active electrode unit 30 or a return electrode unit 60. Spiral inductor 32/62 may include a first or outermost spiral layer 46a, an innermost spiral layer 46b, and at least one intermediate spiral layer 46c. For each spiral 44a, 44b, and 44c, only a first, a second, and a third turn 45a, 45b, 45c, respectively, are shown in FIG. 6A for the sake of clarity, it being understood that each spiral 44a, 44b, and 44c may comprise from about 20 to 150 or more turns. Turns of spirals 44a, 44b, and 44c, including first, second, and third turns 45a, 45b, 45c, as well as additional turns not shown in FIG. 6A, may be generally referred to as turns 45 (see, e.g., FIG. 4A).

Again with reference to FIG. 6A, first or outermost spiral layer 46a may be defined as a layer of spiral inductor 32/62 that is closest to, or in contact with, the patient's body during use of spiral inductor 32/62 (e.g., as a component of active electrode unit 30 or return electrode unit 60). In some embodiments, intermediate layer 46c may represent one or more spiral layers, although only a single intermediate layer 46c is shown in FIG. 6A. In another embodiment, intermediate layer 46c may be omitted to provide a two-layer spiral inductor (see, for example, FIG. 6B). Each layer of spiral inductor 32/62, e.g., outermost layer 46a, innermost layer 46b, and intermediate layer 46c, may comprise spiral 44a, spiral 44b, and spiral 44c, respectively.

With further reference to FIG. 6A, spirals 44a-c may be referred to as a first or outermost spiral 44a, a second or intermediate spiral 44b, and an innermost spiral 44c, respectively. Each spiral 44a, 44b, and 44c may comprise an electrically conductive metal, for example as a metal trace or filament. Spirals 44a, 44b, and 44c may each have the same spiral configuration, e.g., each spiral 44a-c may have the same number of turns, the same pitch, the same trace width, and the same gap width, etc. In an embodiment, spirals 44a, 44b, and 44c may be stacked vertically such that radially corresponding turns of each of spirals 44a, 44b, and 44c are aligned with each other. Spirals 44a, 44b, and 44c may be disposed on a first or outermost support layer 52a, an innermost support layer 52b, and an intermediate support layer 52c, respectively.

With still further reference to FIG. 6A, turns 45 of spirals 44a, 44b, and 44c may be electrically coupled in the following manner: each turn, e.g., first turn 45a, of first spiral 44a may be electrically coupled, in series, to a radially corresponding turn of each successive spiral, i.e., turns 45a' and 45a" of spirals 44b and 44c; and, each turn of innermost spiral 44c, e.g., turn 45a", may be electrically coupled to an adjacent, radially outward turn of first (outermost) spiral 44a, i.e., turn 45b. An exception to this pattern of connection may exist for the radially outermost turn of innermost spiral 44c, since the radially outermost turn lacks an adjacent radially outward turn (e.g., as can be seen from FIG. 6A, turn 45c" could not be coupled to an adjacent, radially outward turn of first spiral 44a, since there is no turn located radially outward from turn 45c").

The same manner of interconnection as described with reference to FIG. 6A may be used for other numbers of vertically stacked spirals 44, each having any number of turns 45. Each turn 45 may be electrically coupled, in series, to a radially corresponding turn of each successive spiral by vertical connections 48, while each turn of innermost spiral 44c may be electrically coupled to an adjacent, radially outward turn of outermost spiral 44a by radial connections 49. In this regard, all radially corresponding turns of adjacent spiral layers may be interconnected by vertical connections 48, whereas radial connections 49 only couple radially non-corresponding turns of innermost and outermost spirals 46b, 46a, respectively.

For the embodiment of FIG. 6A, the interconnection of turns 45 of spiral layers 46a-c to provide a three-layer spiral inductor may be described more specifically as follows:

1) first turn 45a of the first spiral 44a may be electrically coupled to a first turn 45a' of second spiral 44b, 2) first turn 45a' of second spiral 44b may be electrically coupled to a first turn 45a" of third spiral 44c, 3) first turn 45a" of third spiral 44c may be electrically coupled to a second turn 45b of first spiral 44a, 4) second turn 45b of first spiral 44a may be electrically coupled to a second turn 45b' of second spiral 44b, 5) second turn 45b' of second spiral 44b may be electrically coupled to a second turn 45b" of third spiral 44c, and 6) second turn 45b" of third spiral 44c may be electrically coupled to a third turn 45c of first spiral 44a, etc. Thus, first turn 45a, 45a', 45a" of first through third spirals 44a-c, respectively, may jointly define a first set of turns of spiral inductor 32/62; each of a plurality of successive sets of turns of first through third spirals 44a-c may be coupled to each other in series; and each turn 45 of third spiral 44c may be coupled to an adjacent radially outward turn of first spiral 44a. As noted hereinabove, an exception to this connection pattern may exist for the radially outermost turn of third spiral 44c, which naturally lacks a radially outward turn. It is to be understood that the coupling between specific turns enumerated hereinabove may be performed in sequences other than as listed to provide a multi-layer spiral inductor having turns electrically coupled as shown in FIGS. 6A-B.

In describing the manner of interconnectivity of turns 45 for the embodiment of FIG. 6A, first turn 45a, 45a', 45a" of first, second, and third spirals 44a-c, respectively, may represent the radially innermost turn of the first, second, and third spirals 44a-c, respectively; first, second, and third spirals 44a, 44b, and 44c may be vertically stacked on top of each other. First spiral 44a may occupy first or outermost spiral layer 46a; and third spiral 44c may occupy innermost spiral layer 46b (see, FIG. 6A).

For purposes of illustration, each spiral 44a, 44b, and 44c is shown in FIG. 6A as having first, second, and third turns 45a, 45b, 45c, respectively, wherein first turn 45a may be located substantially centrally with respect to each spiral 44a, 44b, and 44c. In practice, each spiral 44a, 44b, and 44c may comprise from about 10 to 200 turns, typically from about 20 to 150 turns, often from about 30 to 150 turns, and usually from about 40 to 120 turns. However, the manner of interconnecting turns of spirals 44a, 44b, and 44c may be as shown in FIG. 6A regardless of the number of turns in each spiral. Namely, each turn, e.g., turn 45a, of first spiral 44a may be electrically coupled, in series, to a radially corresponding turn (turns 45b, 45c) of successive spirals 44c, 44b; and each turn 45 of innermost spiral 44c may be electrically coupled to an adjacent, radially outward turn 45 of first spiral 44a, with the proviso (as noted above) that a radially outermost turn of innermost spiral 44c is not so coupled to an adjacent radially outward turn of first spiral 44a.

Figure 6B:
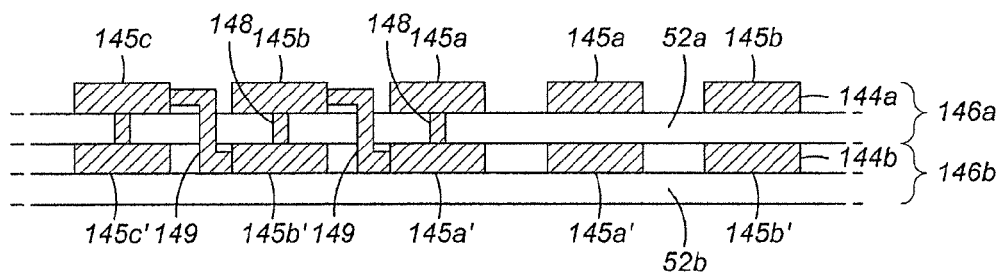
FIG. 6B schematically represents a multi-layer spiral inductor, including a plurality of vertically stacked spirals, showing connections between turns of each spiral, as seen in plan view, according to another embodiment of the invention.

FIG. 6B schematically represents a central portion of a multi-layer spiral inductor 32/62, including two stacked spirals, according to another embodiment of the invention. Spiral inductor 32/62 of FIG. 6B may include a first or outermost spiral 144a and a second or innermost spiral 144b. Turns of first and second spirals 144a, 144b including first and second turns 145a, 145b, as well as additional turns not shown in FIG. 6B, may be referred to herein generically as turns "45" (see, e.g., FIG. 4A). In the spiral inductor 32/62 of FIG. 6B, turns 45 of spirals 144a, 144b may be interconnected between layers 46a and 46b as follows:

1) first turn 145a of first spiral 144a may be electrically coupled to a first turn 145a' of second spiral 144b, 2) first turn 145a' of second spiral 144b may be electrically coupled to a second turn 145b of first spiral 144a, 3) second turn 145b of first spiral 144a may be electrically coupled to a second turn 145b' of second spiral 144b, and 4) second turn 145b' of second spiral 144b may be electrically coupled to a third turn 145c of first spiral 144a, etc. It is to be understood that the coupling between specific turns enumerated hereinabove may be performed in sequences other than as listed to provide a multi-layer spiral inductor having turns electrically coupled as shown in FIGS. 6A-B.

With further reference to FIG. 6B, radially corresponding turns of first and second spirals 144a, 144b may be interconnected by vertical connections 148, while connection between turns of second spiral 144b and a radially outer turn of first spiral 144a (i.e., between radially non-corresponding turns) may be by radial connections 149. First turn 145a, 145a' of first and second spirals 144a, 144b, respectively, may jointly define a first set of turns of spiral inductor 32/62. Each of a plurality of successive sets of turns of first and second spirals 144a, 144b may be electrically coupled to each other, and each turn of second spiral 144b may be coupled to an adjacent radially outward turn of first spiral 144a, with the proviso that the radially outermost turn of second spiral 144b lacks an adjacent radially outward turn. It can be seen that the interconnection of turns 45 of the two-layer spiral inductor 32/62 of FIG. 6B follows the same general pattern of electrical coupling as for the embodiment of FIG. 6A.

Figure 7A:
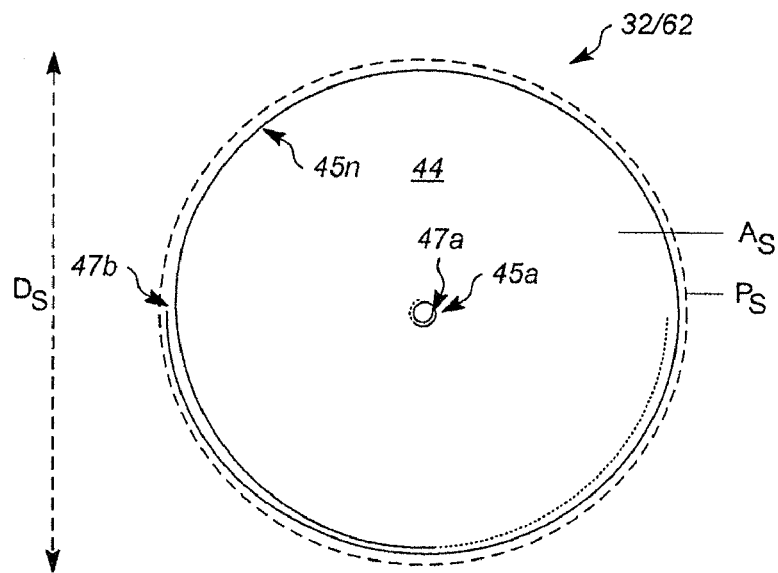
FIG. 7A schematically represents a spiral inductor having a substantially circular or oval configuration, as seen in plan view, according to another embodiment of the invention.

FIG. 7A schematically represents a spiral inductor, as seen in plan view. Spiral inductor 32/62 of FIG. 7A may have a substantially circular or oval configuration. Spiral inductor 32/62 may include a spiral trace 44 of electrically conductive metal having an inner terminus 47a and an outer terminus 47b. For clarity, sections of the spiral trace 44 that are between the terminuses are not shown in FIG. 7A. Spiral inductor 32/62 may include a plurality of turns, from a first turn 45a (radially innermost) to an nth turn 45n (radially outermost). In an embodiment, n may be from about 10 to 200 or more, substantially as described hereinabove. Spiral inductor 32/62 may have a perimeter, Ps, and an external surface area As defined by the perimeter. The electrically conductive metal of spiral 44 may occupy at least about 50% of a total surface area As, that is to say, at least about 50 percent (%) of the external surface area of spiral inductor 32/62 may be occupied by spiral 44. Typically, electrically conductive metal of spiral 44 may occupy from about 60 to 99% of external surface area, As; usually from about 70 to 99% of external surface area, As; often from about 75 to 98% of external surface area, As; and in some embodiments electrically conductive metal of spiral 44 may occupy from about 85% to 97% of external surface area, As. Spiral 44 may have a diameter, Ds, typically in the range of from about 2 to 0.1 cm, usually from about 12 to 0.2 cm, and often from about 10 to 0.4 cm.

Figure 7B:
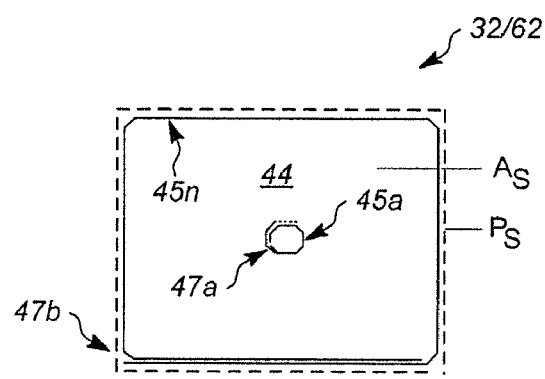
FIG. 7B schematically represents a spiral inductor having a substantially square or rectangular configuration, as seen in plan view, according to another embodiment of the invention.

FIG. 7B schematically represents a spiral inductor. Spiral inductor 32/62 may include a spiral trace 44 of electrically conductive metal having an inner terminus 47a, an outer terminus 47b, and a plurality of turns, 45a-n, substantially as described for the embodiment of FIG. 7A. For clarity, sections of the spiral trace 44 that are between the terminuses are not shown in FIG. 7B. Spiral inductor 32/62 of FIG. 7B may have a substantially square or rectangular configuration, a perimeter, Ps, and a surface area As defined by the perimeter. Spiral inductor 32/62 may include a spiral trace 44 of electrically conductive metal. Spiral trace 44 may occupy a percentage of surface area, As generally as described with reference to FIG. 7A.

In an embodiment, spiral inductors 32/62 of FIGS. 7A-B may comprise a single spiral 44 which may be at least substantially planar. In another embodiment, spiral inductors 32/62 of FIGS. 7A-B may comprise a plurality of vertically stacked spirals 44, wherein each of the plurality of spirals 44 may be at least substantially planar.

Spiral Inductors for Active Electrode Applications

Figure 8:
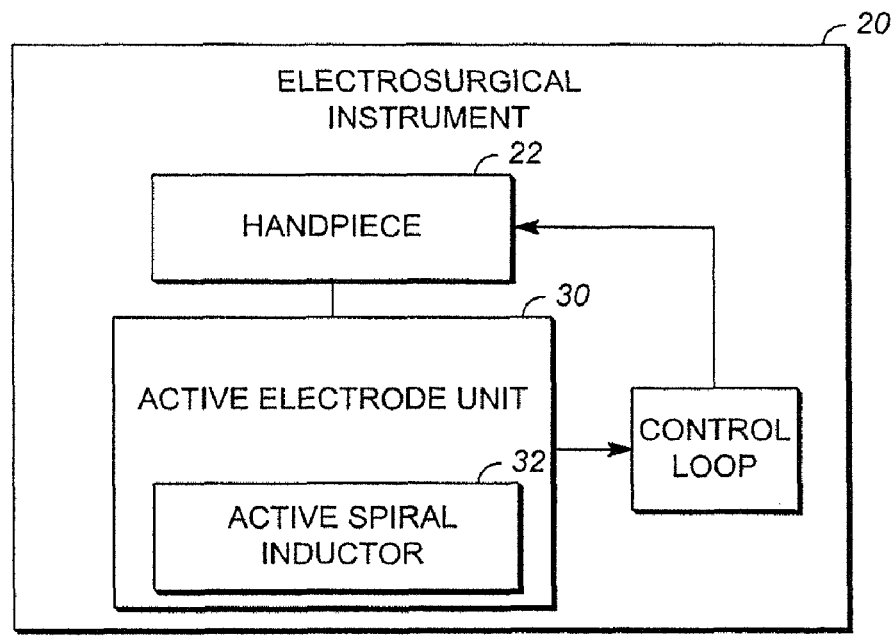
FIG. 8 is a block diagram schematically representing an electro-surgical apparatus including an active electrode unit having a spiral inductor, according to an embodiment of the invention.

FIG. 8 is a block diagram schematically representing an electro-surgical instrument, according to another embodiment of the invention. Electro-surgical instrument 20 may include a handpiece 22, an active electrode unit 30 and a control loop 25. Active electrode unit 30 may include an active spiral inductor 32. Electro-surgical instrument 20 may be coupled to power supply 15 (see, e.g., FIG. 2) to form apparatus configured for the application of electrical energy, via spiral inductor 32, to a target tissue of a patient. Electro-surgical instrument 20, active electrode unit 30, and active spiral inductor 32 may have various other features, elements, and characteristics substantially as described herein for various embodiments of the invention.

Figure 9A:
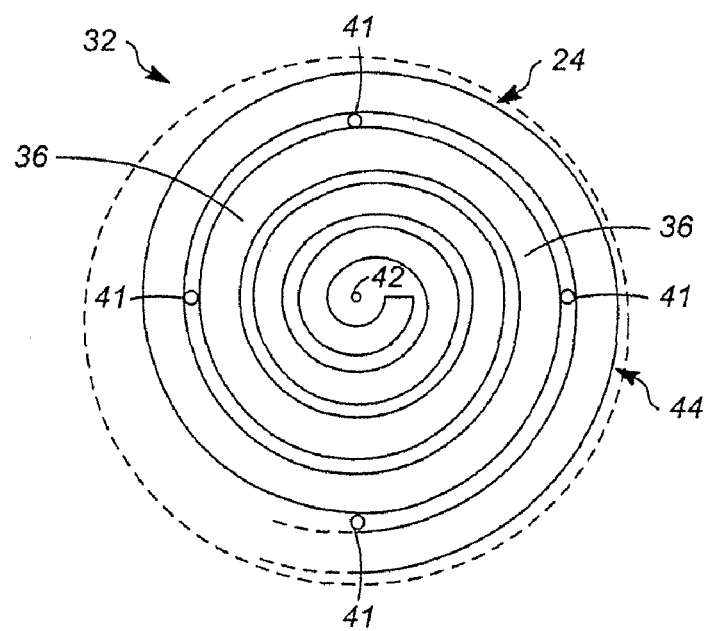
FIG. 9A schematically represents a spiral inductor for an active electrode unit, as seen in plan view, according to another embodiment of the invention.

FIG. 9A schematically represents a spiral inductor for an active electrode unit, as seen in plan view, according to an embodiment of the invention. Active spiral inductor 32 may comprise an electrically conductive metal spiral 44 (see, e.g., FIGS. 4A-C). As an example, spiral 44 may comprise a spiral trace of electrically conductive metal, such as Cu, Al, or various alloys. In an embodiment, spiral 44 may comprise a filament of the electrically conductive metal. In an embodiment, spiral 44 may be formed by a printing process or a printing-like process. An external surface 42a of spiral 44 may define a treatment face 36 of spiral inductor 32 and active electrode unit 30.

Only a radially inner portion of spiral 44 is shown in FIG. 9A, whereas spiral 44 in its entirety may include many more turns. For example, in an embodiment spiral 44 may have from about 10 to 200 turns, typically 20 to 150 turns, often from about 30 to 150 turns, and usually from about 40 to 120 turns. Spiral 44 may have a variable or constant pitch between adjacent turns (see, e.g., FIGS. 4A-C).

Spiral 44 may be disposed on a support layer 24. Support layer 24 may comprise an electrically insulating or dielectric material. Examples include, but are not limited to, Teflon, Polyamide, FR4, G10, Nylon, Polyester, Kapton, Silicone, or Rubber. In an embodiment, support layer 24 may be at least substantially equivalent to one of support layers 52a-c (see, FIGS. 6A-B). In use, spiral 44 may be disposed between support layer 24 and the patient's body. Active spiral inductor 32 may be configured for evenly distributing electric current density thereover via self-inductance of spiral 44. Active spiral inductor 32 may be configured for selectively heating a target tissue of the patient's body and for providing a tissue-altering effect on the target tissue.

Figure 9B:
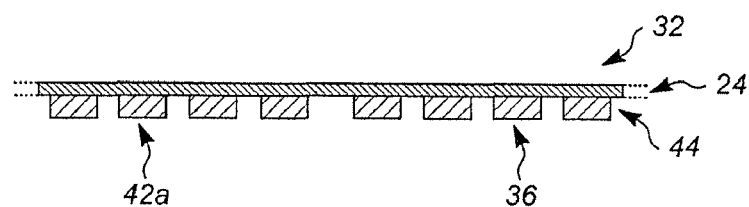
FIG. 9B schematically represents a spiral inductor for an active electrode unit, as seen in side view, according to another embodiment of the invention.

FIG. 9B schematically represents a portion of a spiral inductor 32 for an active electrode, as seen in side view, according to an embodiment of the invention. (In comparison with FIG. 9A, which shows spiral 44 disposed on top of support layer 24, FIG. 9B is shown as being inverted.) Spiral inductor 32 may be at least substantially planar. In an embodiment, spiral inductor 32 may comprise a spiral 44. Spiral 44 may include an external surface 42a. External surface 42a may be a bare metal surface of electrically conductive metal spiral 44. External surface 42a of spiral 44 may define a treatment face 36. External surface 42a and treatment face 36 may be configured for contacting a patient's body (see, e.g., FIG. 14). Treatment face 36 may be at least substantially planar.

Figure 9C:
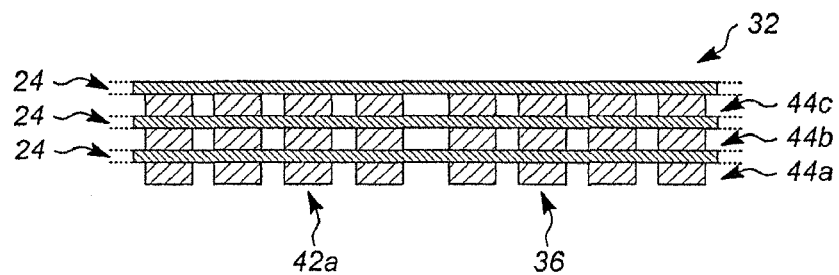
FIG. 9C schematically represents a multi-layer spiral inductor including a plurality of vertically stacked spirals, as seen in side view, according to another embodiment of the invention.

FIG. 9C schematically represents a multi-layer spiral inductor for an active electrode unit, as seen in side view, according to an embodiment of the invention. As shown, active spiral inductor 32 may include a plurality of vertically stacked spirals 44a-c. Spiral 44a may be an outermost spiral 44, while spiral 44c may be referred to as an innermost spiral. Spiral 44b may be referred to as an intermediate spiral. In use, spiral 44a may be closest to, or in contact with a patient's body, while spiral 44c may be the furthest from the patient's body. Each spiral 44a-c may be disposed on a corresponding support layer 24. An external surface 42a of outermost spiral 44a may define a treatment face 36 of active spiral inductor 32. Other numbers of spiral layers 46a-c are also within the scope of the invention.

Figure 10A:
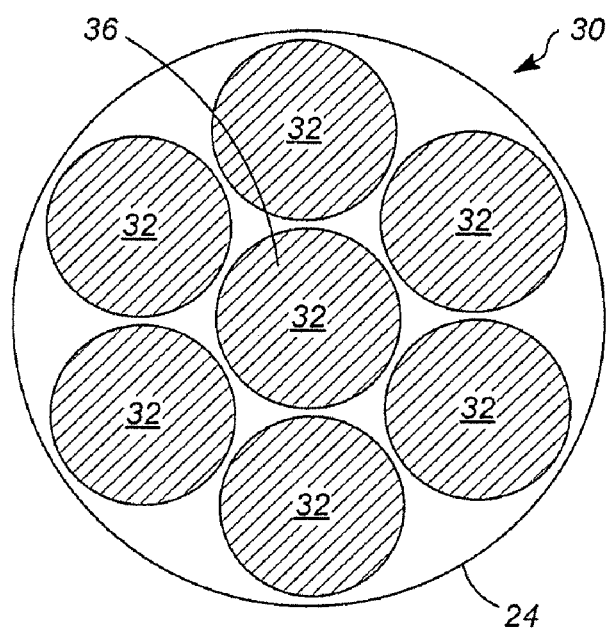
FIG. 10A schematically represents an active electrode unit including a treatment face defined by a plurality of co-planar spiral inductors, as seen in plan view, according to another embodiment of the invention.
Figure 10B:
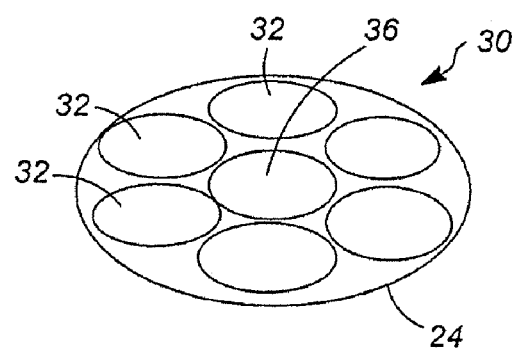
FIG. 10B schematically represents the active electrode unit of FIG. 10A, as seen in perspective view, according to another embodiment of the invention.

FIG. 10A schematically represents an active electrode unit, as seen in plan view, and FIG. 10B shows the active electrode unit of FIG. 10A in perspective view, according to another embodiment of the invention. Active electrode unit 30 may include a plurality of active spiral inductors 32. Active spiral inductors 32 may be at least substantially co-planar, or horizontally arranged, on support layer 24. The external surface 42a (see, e.g., FIG. 9B) of the plurality of spiral inductors 32 may jointly define a treatment face 36. Treatment face 36 may be at least substantially planar. Treatment face 36 may be configured for contacting a patient's body, and for applying electrically energy to a target tissue of the patient's body. Active electrode unit 30 may be coupled to power supply 15 to provide an electrosurgical apparatus configured for independently energizing each of spiral inductors 32 of active electrode unit 30. Active electrode unit 30 and power supply 15 may be configured for sequentially energizing spiral inductors 32. Each of the sequentially energized spiral inductors 32 may be energized for various time periods. In an embodiment, a sequence and/or period of energization of spiral inductors 32 may be based on a temperature-related feedback mechanism.

As shown in FIG. 10A, each active spiral inductor 32 may be substantially circular in configuration; however, other configurations are also within the scope of the invention. Although active electrode unit 30 is shown as having seven (7) active spiral inductors 32, other numbers and arrangements of active spiral inductors 32 are also within the scope of the invention.

Figure 11:
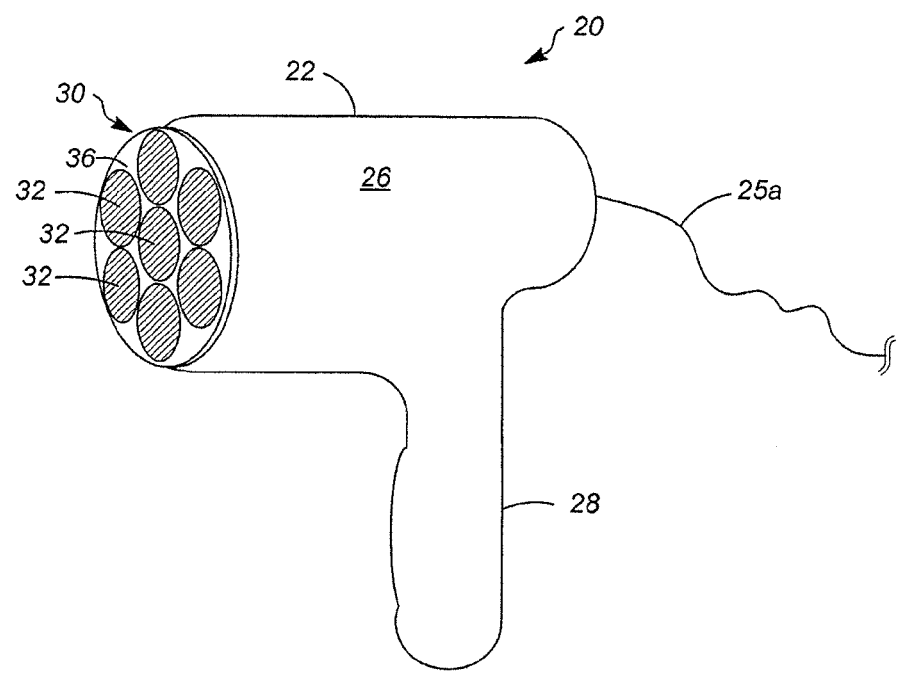
FIG. 11 schematically represents an electro-surgical apparatus including a plurality of spiral inductors, according to another embodiment of the invention.

FIG. 11 schematically represents an electrosurgical instrument, according to another embodiment of the invention. Electrosurgical instrument 20 may include a handpiece 22 and an active electrode unit 30. Active electrode unit 30 may include a plurality of spiral inductors 32. Active spiral inductors 32 may be at least substantially co-planar, such that an external surface 42a of spiral inductors 32 may jointly define a treatment face 36. A cord or cable 25a may be coupled to handpiece 22 for electrically coupling active electrode unit 30 to a power supply (see, e.g., FIGS. 1, 2, and 14). Handpiece 22 may include a housing 26 having a handle 28. Handpiece 22 may be grasped by handle 28 for guiding or moving active spiral inductors 32 and treatment face 36 relative to a treatment area of a patient's body, skin, or target tissue to be treated by electrosurgical instrument 20. Active electrode unit 30 of FIG. 11 may have other features and elements substantially as described with reference to FIGS. 10A-B. Other configurations for handpiece 22, including housing 26 and handle 28, are also within the scope of the invention.

It should be understood that the particular embodiments of the invention described in this application have been provided by way of example and that other modifications may occur to those skilled in the art without departing from the scope and spirit of the invention as express in the appended claims and their equivalents.

What is claimed is:

1. An electro-surgical system for treating a patient, the system comprising:
    an electrode assembly that includes at least one electrode for contacting a target region of the skin of a patient, wherein each of the at least one electrodes includes at least one edge temperature sensor at an edge region of the electrode and configured to generate a corresponding edge temperature signal and at least one center temperature sensor at a center region of the electrode and configured to generate a corresponding center temperature signal;
    a power generator configured to provide RF power to the electrode assembly at an operating frequency; and
    a control unit adapted to receive the edge temperature signal and the center temperature signal, the control unit configured to provide a frequency control signal to the power generator such that,
    in the event that the edge temperature of the electrode is high compared to the center temperature of the electrode, then the frequency control signal causes the power generator to increase the operating frequency thereby driving heat to the center region of the electrode, and
    in the event that the center temperature of the electrode is high compared to the edge temperature of the electrode, then the frequency control signal causes the power generator to decrease the operating frequency thereby driving heat to the edge region of the electrode.

2. An electro-surgical system as in claim 1, and wherein the control unit utilizes a state machine for providing the frequency control signal.

3. An electro-surgical system as in claim 1, and wherein the control unit utilizes a proportional-integral-derivative (PID) algorithm for providing the frequency control signal.

4. An electro-surgical system as in claim 1, and wherein the at least one electrode is spiral-shaped.

5. A method of treating a patient utilizing an electro-surgical system that comprises an electrode assembly that includes at least one electrode for contacting a target region of the skin of the patient and a power generator configured to provide RF power to the electrode assembly at an operating frequency, the method comprising:
    providing the electrode with at least one edge temperature sensor at an edge region of the electrode and configured to generate an edge temperature signal corresponding thereto;
    providing the electrode with at least one center temperature sensor at a center region of the electrode and configured to generate a center temperature signal corresponding thereto;
    monitoring the edge temperature signal and the center temperature signal; and
    in the event that edge temperature of the electrode is high compared to the center temperature of the electrode, providing a frequency control signal to the power generator that causes the power generator to increase the operating frequency thereby driving heat to the center region of the electrode; and
    in the event that the center temperature of the electrode is high compared to the edge temperature of the electrode, providing a frequency control signal to the power generator that causes the power generator to decrease the operating frequency thereby driving heat to the edge region of the electrode.

6. A method as in claim 5, and further comprising:
    utilizing a state machine to generate the frequency control signal.

7. A method as in claim 5, and further comprising:
    utilizing a proportional-integral-derivative (PID) algorithm to generate the frequency control signal.

8. A method as in claim 5, and wherein the at least one electrode is spiral-shaped.

* * * * *